United States Patent
Intravartolo et al.

(10) Patent No.: US 7,214,219 B2
(45) Date of Patent: May 8, 2007

(54) REMOVAL STRING ATTACHMENT FOR INTRAVAGINAL DEVICES

(75) Inventors: Antoinette Intravartolo, Monroe Township, NJ (US); Lai-Hing Louie, Kendall Park, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 264 days.

(21) Appl. No.: 10/640,710

(22) Filed: Aug. 13, 2003

(65) Prior Publication Data
US 2005/0192554 A1    Sep. 1, 2005

Related U.S. Application Data

(62) Division of application No. 10/373,444, filed on Feb. 25, 2003, now abandoned, which is a division of application No. 09/874,451, filed on Jun. 5, 2001, now abandoned.

(60) Provisional application No. 60/280,299, filed on Mar. 30, 2001.

(51) Int. Cl.
   *A61F 13/20* (2006.01)
(52) U.S. Cl. ............... 604/385.18; 604/11; 604/13; 604/385.17; 604/904
(58) Field of Classification Search ........... 604/385.17, 604/385.18, 904, 367, 369, 374, 11–18
   See application file for complete search history.

(56) References Cited

U.S. PATENT DOCUMENTS

| | | | |
|---|---|---|---|
| 1,731,665 A | 10/1929 | Huebsch | |
| 2,264,586 A | 12/1941 | Ross | |
| 2,330,257 A | 9/1943 | Bailey | |
| 2,710,007 A | 6/1955 | Greiner et al. | |
| 3,812,856 A * | 5/1974 | Duncan et al. | 604/364 |
| 3,815,601 A * | 6/1974 | Schaefer | 604/15 |
| 4,266,546 A * | 5/1981 | Roland et al. | 604/365 |
| 4,278,088 A | 7/1981 | Reeves et al. | |
| 4,341,214 A | 7/1982 | Fries et al. | |
| 4,475,911 A | 10/1984 | Gellert | |
| 4,710,186 A | 12/1987 | DeRossett et al. | |
| 4,743,237 A | 5/1988 | Sweere | |
| 5,273,521 A * | 12/1993 | Peiler et al. | 604/13 |
| 5,383,891 A * | 1/1995 | Walker | 606/196 |
| 5,548,835 A | 8/1996 | Sasaki | |
| 5,567,376 A | 10/1996 | Turi et al. | |
| 5,807,372 A * | 9/1998 | Balzar | 604/385.18 |
| 6,142,928 A | 11/2000 | Zunker et al. | |
| 6,595,974 B1 * | 7/2003 | Pauley et al. | 604/385.18 |
| 2001/0012929 A1 | 8/2001 | Suga et al. | |

FOREIGN PATENT DOCUMENTS

EP      0 610 951 A      8/1994
WO   WO 02/056811 A     7/2002

* cited by examiner

*Primary Examiner*—Jacqueline F. Stephens

(57) ABSTRACT

An intravaginal device having an overwrap containing an enclosed material, and a withdrawal string passing through a portion of the overwrap formed into a loop, the withdrawal string enabling a user to remove the intravaginal device after use.

3 Claims, 4 Drawing Sheets

REMOVAL STRING ATTACHMENT FOR INTRAVAGINAL DEVICES

CROSS-REFERENCE TO RELATED APPLICATIONS

The present application is a divisional of Ser. No. 10/373,444, filed Feb. 25, 2003, (hereby incorporated by reference herein) now abandoned, which is a divisional of Ser. No. 09/874,451, filed Jun. 5, 2001 (hereby incorporated by reference herein) now abandoned, which claims priority of provisional application Ser. No. 60/280,299, filed Mar. 30, 2001 (hereby incorporated by reference).

FIELD OF THE INVENTION

The invention relates to a novel string attachment for intravaginal devices. More particularly, the present invention relates to removal string attachment for a catamenial tampon.

BACKGROUND OF THE INVENTION

Intravaginal devices are in common use by women for a variety of reasons. The most common application is a catamenial tampon for the retention of fluid or menses discharged during the menstrual cycle. Other intravaginal devices include urinary incontinence devices, collection cups, birth control devices, and inflation devices used to block menstrual fluid.

Commercial catamenial tampons are often comprised of an absorbent body of moderately compressed fibers, and these tampons are generally in the shape of a cylinder or a bullet. A second type is a tampon that is more prevalent in the patent art than it is commercially available has relatively loose absorbent material encased within a porous overwrap. This is commonly known as a bag-type tampon.

Methods of attachment of the removal string to intravaginal devices, including conventional and bag-type tampons, have included passing a string through the device and knotting the string after it has passed through the device ("pierce and loop"). An example of this type can be seen in U.S. Pat. No. 6,142,928 (Zunker et al.). Another removal system includes knotting the withdrawal string about the trailing end of the intravaginal device. Both systems, however, are subject to failure if the knot is not perfectly formed or becomes untied.

In addition to the methods already disclosed, U.S. Pat. No. 3,815,601 (Schaefer) and U.S. Pat. No. 4,475,911 (Gellert) disclose attaching the removal string to the intravaginal device by other ways, including threading a doubled string through the overwrap and fixing the removal string to the surface of the overwrap by sewing or bonding.

U.S. Pat. No. 1,731,665 (Huebsch) and U.S. Pat. No. 2,710,007 (Greiner et al.) both disclose extending the overwrap and using it at the trailing end as a removal string.

U.S. Pat. No. 4,278,088 (Reeves et al.) discloses a bag-type tampon containing discrete pieces of absorbent. The bag is sealed and the removal string attached by any conventional means such as heat sealing, tying of the bag with the removal string or adhesive sealing and/or mounting of the string.

U.S. Pat. No. 4,341,214 (Fries et al.) discloses a bulky catamenial tampon where the trailing end of the sleeve is gathered and closed by a string. Upon pulling the string for removing the tampon, the gathered end forms a tapered configuration that aids in comfort during removal.

U.S. Pat. No. 4,743,237 (Sweere) discloses bonding the removal string with the inner surface of the thermoplastic gauze overwrap at the trailing end. The trailing end may then be formed into an accordion-like fold.

U.S. Pat. No. 2,330,257 (Bailey) discloses using the removal string to constrict the lower end of the tampon to facilitate the withdrawal of the tampon without irritation.

EP 0 610 951 (Van Iten) discloses an encapsulated catamenial tampon in which the tampon itself is constructed of a plurality of compressed absorbent cones nested together and attached together by a withdrawal string.

Some of the attachment methods described are subject to failure during removal. Others involve complicated methods of attaching the removal strings to the intravaginal device.

What is needed, therefore, is a simple way to securely attach the removal string while ensuring comfort and easy removal of the device from the vagina.

SUMMARY OF THE INVENTION

An intravaginal device having an insertable material enclosed by an overwrap, the overwrap having a loop formed therein, and a withdrawal string passing through the loop to enable a user to remove the intravaginal device after use.

DETAILED DESCRIPTION OF THE INVENTION

In general, this invention relates to an intravaginal device having an overwrap, an insertable material contained therein, and a removal string attached to the overwrap.

The intravaginal device may be any device that is inserted into the vaginal canal. Examples of intravaginal devices include conventional tampons, urinary incontinence devices, birth control devices (IUD), inflation devices or blocking devices, or menstrual cups.

In a preferred embodiment the intravaginal device is a bag-type tampon. As shown in the figures, bag-type tampon 10 has overwrap 20, enclosed material 30 and removal string 40.

Figure 1A:
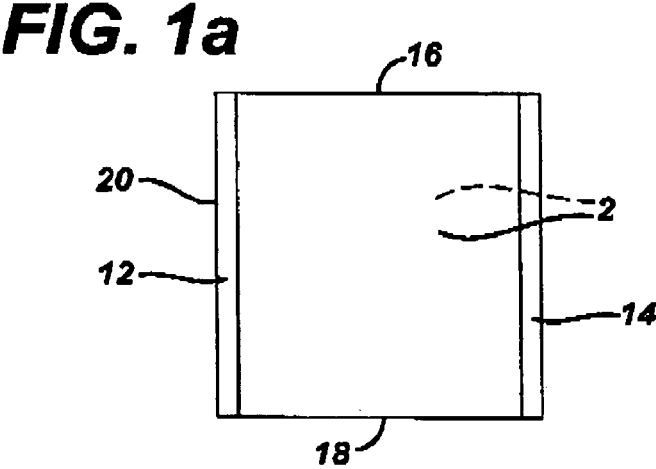
FIGS. 1a–c show steps in a process of forming the overwrap prior to filling with insertable material.
Figure 1B:
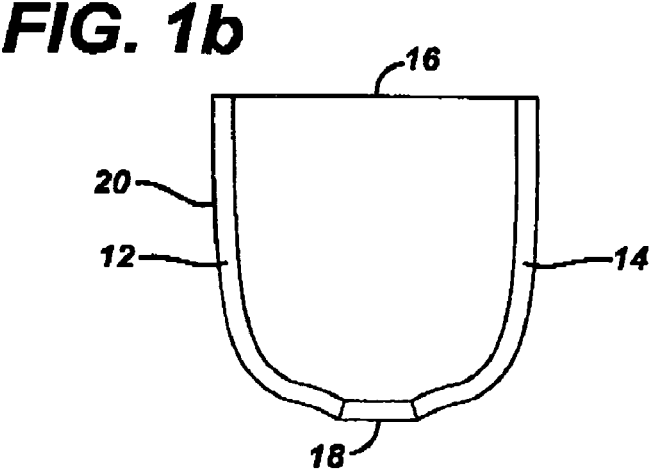
Figure 1C:
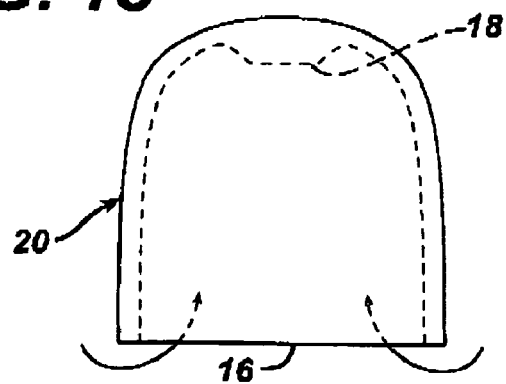
Figure 2:
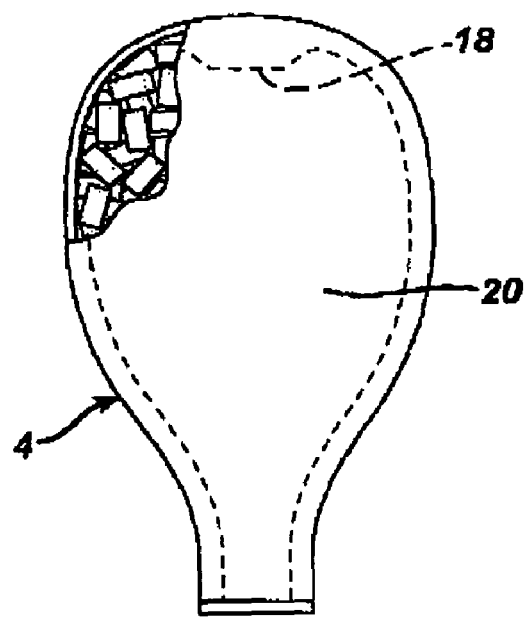
FIG. 2 is an elevational view of an intravaginal device having a closed "fill" end.
Figure 3:
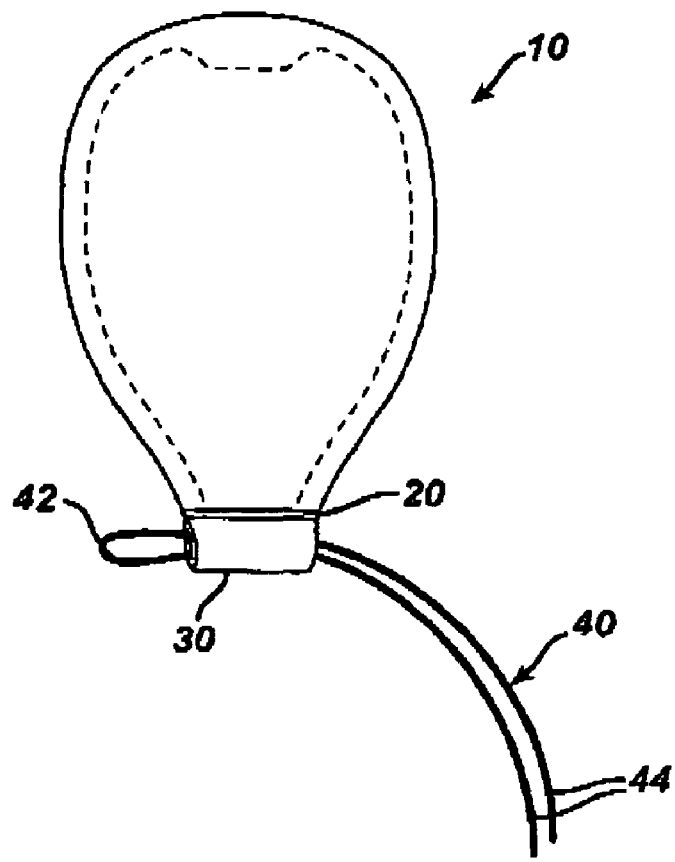
FIG. 3 is an elevational view showing the lower sealed portion looped and the string placed through the loop.
Figure 4:
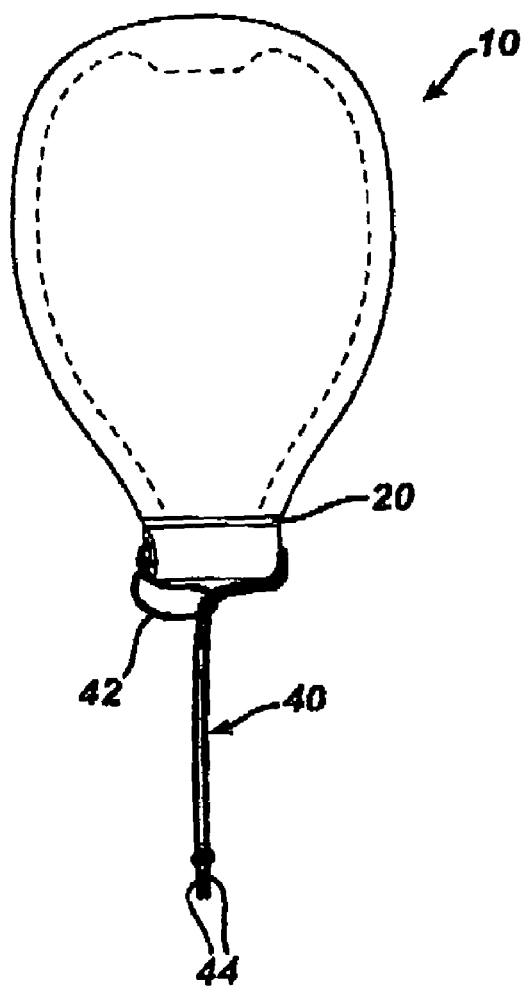
FIG. 4 is an elevational view of the intravaginal device according to the present invention.

FIGS. 1–4 show details of a preferred embodiment of the present invention. FIGS. 1a–1c show the formation of a bag-type sack into which the enclosed material is placed. FIG. 2 shows the bag-type tampon once the end is sealed, and FIGS. 3 and 4 show attachment of the string.

In a preferred embodiment, the overwrap is liquid permeable and is cut from two sheets of material 2 that are sealed along their lateral sides 12, 14, forming first open end 16 and second open end 18. FIG. 1b shows second open end 18 gathered and closed. Resultant bag 4 is then inverted (FIG. 1c) and filled with the enclosed material 20. First end 16 of the bag is gathered and closed across the edge 22 of the previously open end (FIG. 2).

In another preferred embodiment, one sheet of material may be used to form the overwrap. The single sheet of material may be folded over once, e.g., at the second end, and it can be gathered. Alternately, a single piece of material may be folded such that a single seam running from the upper portion to the lower portion is formed. In this embodiment, two folds could form lateral sides 12 and 14, although the seam could also form one of the lateral sides. Regardless of whether the seam forms a lateral side, the 1st and 2nd ends of this embodiment would be open prior to gathering and closing.

In still another embodiment, a sheet cut into a circular shape (not shown) may be gathered about the edges such that the gathered portion could be folded to form the loop. Likewise, any type of tubular or sack-like material could also be gathered at one end and folded to form a loop. The resultant sack could also be pleated laterally to form a "tea-bag" type of enclosure.

Looking at FIG. 3, first end 16 is then folded and edge 22 is affixed to the overwrap, forming a loop 30. String 40 may then be threaded through loop 30 of the overwrap. Alternately, string 40 may be laid across the lower portion 18 prior to the forming of overwrap loop 30.

In a preferred embodiment, a long piece of string 40 is selected and doubled over, forming string loop 42. This is also shown in FIG. 3.

Free ends 44 of the string 40 can then be fed through formed string loop 42 and pulled tight to form a hitch. This is shown in FIG. 4. In a preferred embodiment, free ends 44 are further knotted to form a gripping portion to assist in removal.

The removal string is securely attached to the intravaginal device, allowing the user to comfortably remove the absorbent device.

The overwrap or bag-forming material may be any sheet-like material that is capable of containing the enclosed material within the bag. A representative, non-limiting list of suitable overwrap materials include woven, nonwoven, and knit textiles; plastic films, including impermeable films and permeable apertured films; polymeric nets; and the like. Preferably, the sheet-like materials are soft, flexible, and have small apertures or pores therethrough. Additional desirable features can include biodegradability.

Useful overwrap materials enable easy bag formation and closure. Therefore, qualities such as thermobondability, high tensile strength, high masking effect to prevent users from noticing the absorbent material and softness are desirable. In particular, materials such as polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. If the overwrap is liquid impermeable, it serves to block body fluids from contacting the insertable material. The overwrap may also be micro-embossed. If the overwrap material has pores or apertures, they should be small enough to keep small pieces and/or fibers of the enclosed material from escaping through the overwrap and to prevent edges or corners of pieces from protruding through the overwrap. Protrusion of pieces through apertures may interfere with ejection of intravaginal device from an applicator, if used. Examples of films having apertures include for example, three-dimensional apertured films, as disclosed in Turi et al, U.S. Pat. No. 5,567,376, and two-dimensional reticulated film, such as that described in DeRossett et al., U.S. Pat. No. 4,710,186 may also be used. Thus, the outer surface of the overwrap should be as smooth and have as low a coefficient of friction as possible. This provides at least two benefits: (1) the force required to eject the intravaginal device is reduced, and (2) it reduces the damage otherwise caused by scraping of soft, tender vaginal tissue during insertion, wearing and removal.

If the overwrap of the intravaginal device is liquid permeable, fluid can penetrate into and be absorbed by the enclosed material. Alternatively, the overwrap can be liquid impermeable if the intravaginal device is not designed to absorb fluid. An example of such a device, a urinary incontinence device, is disclosed in U.S. Pat. No. 6,142,928.

Regardless of whether the overwrap is liquid permeable or liquid impermeable, the overwrap must be strong enough to prevent rupturing during handling, insertion, removal and from vaginal pressures during use.

The overwrap may be attached to itself in one or more locations in the formation of its sack-like structure and/or its loop. Such attachment or adherence may be by any known means, including, for example, adhesive, ultrasonics, co-embossing, thermobonding, mechanical bonding, and the like. In a preferred embodiment, the overwrap is formed of materials capable of being thermobonded together. Additionally, the material may formed of two different materials having different melting points.

The removal string may be formed of any suitable material. Examples of materials suitable for use as removal string include any string sufficiently strong enough to withstand removal forces used to removal the tampon from the body cavity. Typical of such materials are cord or strings formed of cotton as well as of plastics such as rayon, polypropylene, polyester, nylon or blends thereof. Additionally, materials may be elastic or extensible without being elastic. The cords and strings are less likely to wick fluid if treated with a repellent such as wax or silicone. However, a cotton, rayon and polyester are the preferred materials as they are low in price, soft and strong. The term "string" as used herein is intended to include groups of fibers or strands, such as twisted cotton, as well as monofilament polymer strands.

The enclosed material may be any absorbent or non-absorbent material used in the formation of intravaginal devices. The material may be present in an aggregate of particles, a rolled blank or pledget, a folded form, or a solid shaped form.

Examples of absorbent materials used in intravaginal devices include an aggregate of separate pieces of low modulus, resilient, absorbent foam (the aggregate may include an ancillary absorbent material), superabsorbent polymers, discrete pieces of a compressed dry shape-retaining absorbent rigid paper-like mat made at least partially from compressible cellulosic fibers, foams including foam-fiber composites that can be cut into specific shapes such as cylinders or ovoids or rolled and/or folded into specific shapes such as cylinders and tablets formed from compressed fibrous, absorbent material.

The fibrous, absorbent material includes bondable fibers, bondable fiber blends, and/or fibers combined with binding agents. This allows the compressed intravaginal device to remain compressed. Preferably, at least a portion of the fibers is capable of hydrogen bonding. Hydrogen bonding holds the fibers in a compressed form until moisture breaks the bonds. Other bondable fibers may have a bondable surface treatment that is releasable in a moist (water vapor) or aqueous liquid environment. Binding agents may also be used to maintain the compression of the tablets, including without limitation, water-soluble binding agents, waxes, glues and the like.

Preferably fibers include, without limitation, cellulosic fibers and synthetic fibers such as polyesters, polyvinyl alcohols, polyolefins, polyamines, polyamides, polyacrylonitriles, and the like can also be used. A representative, non-limiting list of cellulosic fibers includes natural fibers such as cotton, wood pulp, jute, bagasse, sphagnum, silk, wool, and the like; and processed fibers such as regenerated cellulose, cellulose acetate, cellulose nitrate, rayon, and the like. Preferably, the cellulosic fibers are rayon or cotton, and more preferably, the fibers are rayon.

The fibers can also be multi-limbed, including multi-limbed regenerated cellulosic fiber and multi-limbed polyester or polyolefin fibers. A preferred source of multi-limbed regenerated cellulosic fibers is available as DANUFIL VY viscose rayon fibers from Acordis Ltd., Spondon, England. These fibers are described in detail in Wilkes et al., U.S. Pat. No. 5,458,835, the disclosure of which is hereby incorporated by reference. It is expected that any multi-limbed commercial fiber or even other such fibers not currently commercially available, would be useful in the practice of this invention.

The non-absorbent enclosed material is constructed from materials that exhibit little, and preferably, no absorbent characteristics. The non-absorbent material does not function to absorb bodily fluid. While it is recognized that virtually all materials will absorb some small quantity of moisture, the non-absorbent does not absorb significant quantities of moisture within its structure. Non-absorbent materials include LYCRA®, KEVLAR®, carbon fibers and the like. "LYCRA" and "KEVLAR" are trademarks of E.I. DuPont de Nemours & Company, which has an office at 1007 Market Street, Wilmington, Del. 19801. Bicomponent fibers can also be used.

Additionally, the non-absorbent material could be an absorbent material which has been chemically treated to render it non-absorbent.

The non-absorbent material may also include a resilient member which functions as an incontinence device, birth control device, inflation device or collection cup. The resilient member can be formed from natural materials including natural rubber and wool, and synthetic materials including polyolefins, polyurethanes, polyethylene oxide (PEO), hydrophobic polyvinyl alcohol (PVA) as well as blends thereof. The resilient member can also be made from either an open cell or a closed cell foam.

EXAMPLE

The present invention will be further understood by reference to the following specific Example that is illustrative of the composition, form and method of producing the device of the present invention. It is to be understood that many variations of composition, form and method of producing the device would be apparent to those skilled in the art. The following Example, wherein parts and percentages are by weight unless otherwise indicated, is only illustrative.

Example 1

Bag-type tampons were prepared with the following specifications: the overwrap is made by cutting a piece of approximately 11 inches by 11 inches of ENKA 4128, bicomponent (polyethylene over polyester) fibers available from PGI Nonwovens, Dayton, N.J., USA. The fabric is turned inside out and heat-sealed ¼ inch from the edges on both sides with an "impulse" sealer. One end is gathered and sealed ¼ inch from the edge. The resultant bag is then inverted to enclosed the loose, sealed edges and filled with the absorbent material mixture of 75 wt-% DANUFIL VY multi-limbed rayon fibers and 25 wt-% DANUFIL V rayon fibers which had been compressed into tablet as described in Buzot, U.S. Ser. No. 09/741,718 filed Dec. 20, 2000. The disclosure of which is herein incorporated by reference. The open end of the bag is sealed across the straight end. This end is then gathered, folded up and sealed with the impulse sealer, forming a loop approximately ¼ inch in length. The string is doubled over and fed through the loop. The free ends of the string are fed through the string loop, and pulled tight to form a hitch. The free ends of the string are then knotted together.

Other variations of Example 1 may be made. For example, the string may be placed across the lower portion of the bag prior to sealing and the formation of the bag loop. Additionally, other intravaginal devices such as pledget tampons, pillow type tampons, tampons formed from an aggregate of materials, IUDs, incontinence devices, collection cups or inflation devices may be used in place of absorbent tablets. The intravaginal device would be placed within the bag prior to the sealing of the lower portion. Thus, the bag would form a cover over the intravaginal device. Attachment of the removal string to the bag would allow the user to easily remove the device from the vaginal cavity.

The specification and embodiments above are presented to aid in the complete and non-limiting understanding of the invention disclosed herein. Since many variations and embodiments of the invention can be made without departing from its spirit and scope, the invention resides in the claims hereinafter appended.

The invention claimed is:

1. An intravaginal device comprising an overwrap containing non-absorbent material, and a withdrawal string passing through a portion of the overwrap that is substantially free of the non-absorbent material and formed into a loop, the withdrawal string enabling a user to remove the intravaginal device after use.

2. An intravaginal device comprising an overwrap containing enclosed material, and a withdrawal string passing through a portion of the overwrap that is substantially free of the enclosed material and formed into a loop, the withdrawal string enabling a user to remove the intravaginal device after use, wherein the enclosed material further comprises a resilient member.

3. An intravaginal device comprising an overwrap containing enclosed material, and a withdrawal string passing through a portion of the overwrap that is substantially free of the enclosed material and formed into a loop, the withdrawal string enabling a user to remove the intravaginal device after use, wherein the intravaginal device is an inflation device.

* * * * *